United States Patent
Lakare

(10) Patent No.: US 8,031,917 B2
(45) Date of Patent: Oct. 4, 2011

(54) SYSTEM AND METHOD FOR SMART DISPLAY OF CAD MARKERS

(75) Inventor: Sarang Lakare, Malvern, PA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 1188 days.

(21) Appl. No.: 11/385,211

(22) Filed: Mar. 21, 2006

(65) Prior Publication Data

US 2006/0215894 A1 Sep. 28, 2006

Related U.S. Application Data

(60) Provisional application No. 60/664,419, filed on Mar. 23, 2005.

(51) Int. Cl.
*G06K 9/00* (2006.01)

(52) U.S. Cl. .................................................... 382/128

(58) Field of Classification Search ............... 128/922; 382/110, 128
See application file for complete search history.

(56) References Cited

U.S. PATENT DOCUMENTS

| | | | |
|---|---|---|---|
| 2003/0016850 A1* | 1/2003 | Kaufman et al. | 382/128 |
| 2003/0165262 A1* | 9/2003 | Nishikawa et al. | 382/128 |
| 2004/0252871 A1 | 12/2004 | Tecotzky et al. | |
| 2004/0258291 A1 | 12/2004 | Gustafson et al. | |
| 2005/0002548 A1* | 1/2005 | Novak et al. | 382/128 |
| 2005/0010445 A1* | 1/2005 | Krishnan et al. | 705/2 |
| 2005/0102315 A1* | 5/2005 | Krishnan | 707/102 |
| 2006/0139319 A1* | 6/2006 | Kariathungal et al. | 345/156 |
| 2006/0147099 A1* | 7/2006 | Marshall et al. | 382/128 |

OTHER PUBLICATIONS

International Search Report including Notification of Transmittal of the International Search Report, International Search Report and Written Opinion of the International Searching Authority, PCT Appln No. PCT/US2006/010349, mailed Aug. 21, 2006.

* cited by examiner

*Primary Examiner* — Brian Werner
*Assistant Examiner* — Nirav G Patel
(74) *Attorney, Agent, or Firm* — Peter Withstandley

(57) ABSTRACT

A method for displaying computer aided detection markers from a digitized image includes marking a first set of locations of interest during a first read of the image, producing a first set of markers, receiving a second set of markers of locations of interest on the image from a CAD algorithm, combining the first set of markers with the second set of markers, sorting the combined set of markers according to a predetermined criteria, and presenting the sorted set of markers to a user for a second read of the image.

24 Claims, 2 Drawing Sheets

SYSTEM AND METHOD FOR SMART DISPLAY OF CAD MARKERS

CROSS REFERENCE TO RELATED UNITED STATES APPLICATION

This application claims priority from "Smart Display of CAD Markers Using First Read Knowledge", U.S. Provisional Application No. 60/664,419 of Sarang Lakare, filed Mar. 23, 2005, the contents of which are incorporated herein by reference.

TECHNICAL FIELD

This invention is directed to a smart method of displaying computer aided detection (CAD) results in medical imaging.

DISCUSSION OF THE RELATED ART

The diagnostically superior information available from data acquired from current imaging systems enables the detection of potential problems at earlier and more treatable stages. Given the vast quantity of detailed data acquirable from imaging systems, various algorithms must be developed to efficiently and accurately process image data. With the aid of computers, advances in image processing are generally performed on digital or digitized images.

Digital images are created from an array of numerical values representing a property (such as a grey scale value or magnetic field strength) associable with an anatomical location points referenced by a particular array location. The set of anatomical location points comprises the domain of the image. In 2-D digital images, or slice sections, the discrete array locations are termed pixels. Three-dimensional digital images can be constructed from stacked slice sections through various construction techniques known in the art. The 3-D images are made up of discrete volume elements, also referred to as voxels, composed of pixels from the 2-D images. The pixel or voxel properties can be processed to ascertain various properties about the anatomy of a patient associated with such pixels or voxels. Computer-aided detection systems play a critical role in the analysis and visualization of digital imaging data.

Computer-aided detection (CAD) technology is a recent advance in the field of medical imaging. The CAD technology basically works like a second pair of eyes, reviewing a patient's image data for any abnormalities. If the computer software detects any abnormalities or "regions of interest" on a medical image, it marks them. The radiologist can then go back and review the original image again to determine whether the marked areas are suspicious and require further examination. With the CAD technology, the radiologist still makes the final interpretation of the image.

In essence, the CAD technology works like a "spell-checker". The computer marks abnormalities on the digitized films similar to the way a computer program might alert a writer to a misspelled word. After reviewing the computer's marking, the radiologist can decide whether the marked area is indeed an abnormality that needs follow-up or if the computer has alerted him or her to a normal area, such as a blood vessel, that is no cause for concern. The final interpretation is still made by the radiologist.

Early researchers explored the use of various features to describe and detect lesions. Image processing was a natural tool for this purpose because it provides a set of techniques that enhances features of interest and de-enhances others with the application of many types of filters. Image processing also includes techniques for quantifying visual features and for providing metrics to measure geometric, topologic, or other characteristics by which images are described. These various techniques form the foundations of CAD technology.

A CAD unit typically includes 3 parts: (1) the scanner; (2) the software; and (3) the viewer. The scanner is used to scan and digitize an image, similar to a desktop scanner used to digitally save photographs. Some images already are captured digitally, in which case this step does not apply. The software includes algorithms to analyze the film or image and prompt the radiologist to review areas that may suggest a lesion. The software function displays the images on viewers, such as computer display monitors.

Mammography provides one example of when CAD may be useful because it is a screening modality involving a large volume of images. Projection chest radiography may be another because interpreting such radiographs can also be a high-volume procedure. Yet another example is multi-slice CT, which produce several hundred, if not thousand, images. With any modality in which the radiologist confronts a large volume of imaging information under conditions that may challenge normal perceptual abilities, CAD may be a useful adjunct to traditional image reading.

Mammography can help detect breast cancer at an early stage, when the chances for successful treatment and survival are the greatest. While mammography detects approximately 85% to 90% of breast cancers, mammogram films can be difficult for radiologists to read. Thus, radiologists can occasionally overlook breast cancers that are present on mammogram films. In this situation, CAD technology works as a "second reading" for radiologists, alerting them to areas on films that may require more attention.

When as many features or descriptors as possible have been computed, a decision has to be made whether the object, with all its features, is suggestive enough to be brought to the radiologist's attention. Artificial intelligence (AI) techniques can be used to make these decisions. AI techniques include rule-based codes or expert systems, decision trees, linear or higher-order classifiers, and neural networks.

CAD marks many areas that the radiologist may dismiss, and some of these findings may later be confirmed to be cancer. The CAD algorithm may be able to detect findings that the human eye still cannot perceive on the screening mammogram. Based on clinical studies of the CAD technology, researchers estimate that for every 100,000 breast cancers currently detected with screening mammograms, the CAD technology could result in the detection of an additional 20,500 breast cancers.

Studies performed in early years indicated the need for double readings with human observers rather than computers to conduct the second reading. Most studies showed that sensitivity improved somewhat as a result of double reading. This was another indication that radiologists can fail to notice important findings on images.

Typically, the results from CAD are detection locations or markers that the physician reviews. The time involved in the physician's second read is thus quite dependent both on how many markers are presented for review and how the CAD markers are presented for review. Most current display techniques simply present the markers in a drop down list. The physician can then click on the markers to review each of them. Thus, the manner in which markers are displayed can have a significant impact on the review time.

SUMMARY OF THE INVENTION

Exemplary embodiments of the invention as described herein generally include methods and systems for presenting markers in a way that incorporates prior knowledge from a physician's first read to categorize the markers. CAD results are displayed in such a way that only additional locations found by the CAD algorithm, not marked or previously visited by the physician during the first review are marked by the CAD algorithm.

According to an aspect of the invention, there is provided a method for displaying computer aided detection markers from a digitized image, including providing a digitized image comprising a plurality of intensities corresponding to a domain of points on a 3-dimensional grid, marking a first set of locations of interest during a first read of said image, producing a first set of markers, receiving a second set of markers of locations of interest on said image from said CAD algorithm, combining said first set of markers with said second set of markers, sorting said combined set of markers according to a predetermined criteria, and presenting said sorted set of markers to a user for a second read of said image.

According to a further aspect of the invention, the method includes performing a computer-aided detection (CAD) algorithm on said image.

According to a further aspect of the invention, the method includes storing said first set of markers for comparison with said second set of markers.

According to a further aspect of the invention, the method includes performing a diagnosis based on said sorted set of markers.

According to a further aspect of the invention, sorting said combined set of markers comprises selecting a primary set of markers from said second set of markers comprising those markers detected by said CAD algorithm that are not included in said first set of markers, and selecting a secondary set of markers from said second set of markers comprising those markers detected by said CAD algorithm that are also included in said first set of markers, and presenting said primary set of markers before said secondary set of markers.

According to a further aspect of the invention, the method includes recording the time a user spends reviewing each of said first set of markers.

According to a further aspect of the invention, sorting said combined set of markers comprises sorting the second set of markers according to amount of time spent reviewing a corresponding marker in said first set of markers, and presenting first those markers with the least amount of time.

According to a further aspect of the invention, the method includes displaying said image and said markers on a display monitor.

According to a further aspect of the invention, the method includes storing the region reviewed during the first read.

According to a further aspect of the invention, sorting said combined set of markers comprises selecting a primary set of markers from said second set of markers comprising those markers detected by said CAD algorithm that are pointing to a region of interest not reviewed during the first read, selecting a secondary set of markers from said second set of markers comprising those markers that are detected by said CAD algorithm that are pointing to a region of interest reviewed during the first read, and presenting said primary set of markers before said secondary set of markers.

According to a further aspect of the invention, the method includes presenting for display only those additional markers that were detected by said CAD algorithm.

According to a further aspect of the invention, the method includes presenting for display only those markers detected by said CAD algorithm that were also detected in the first read.

According to a further aspect of the invention, the time spent reviewing said first set of markers is determined based on the user's interaction with the locations of interest marked by said markers, including using one or more of zooming, panning, and eye-tracking tools.

According to a further aspect of the invention, the reviewed region is detected based on the user's interaction with the locations of interest marked by said markers, including using one or more of zooming, panning, and eye-tracking tools.

According to another aspect of the invention, there is provided a program storage device readable by a computer, tangibly embodying a program of instructions executable by the computer to perform the method steps for displaying computer aided detection markers from a digitized image.

DETAILED DESCRIPTION OF THE PREFERRED EMBODIMENTS

Figure 1:
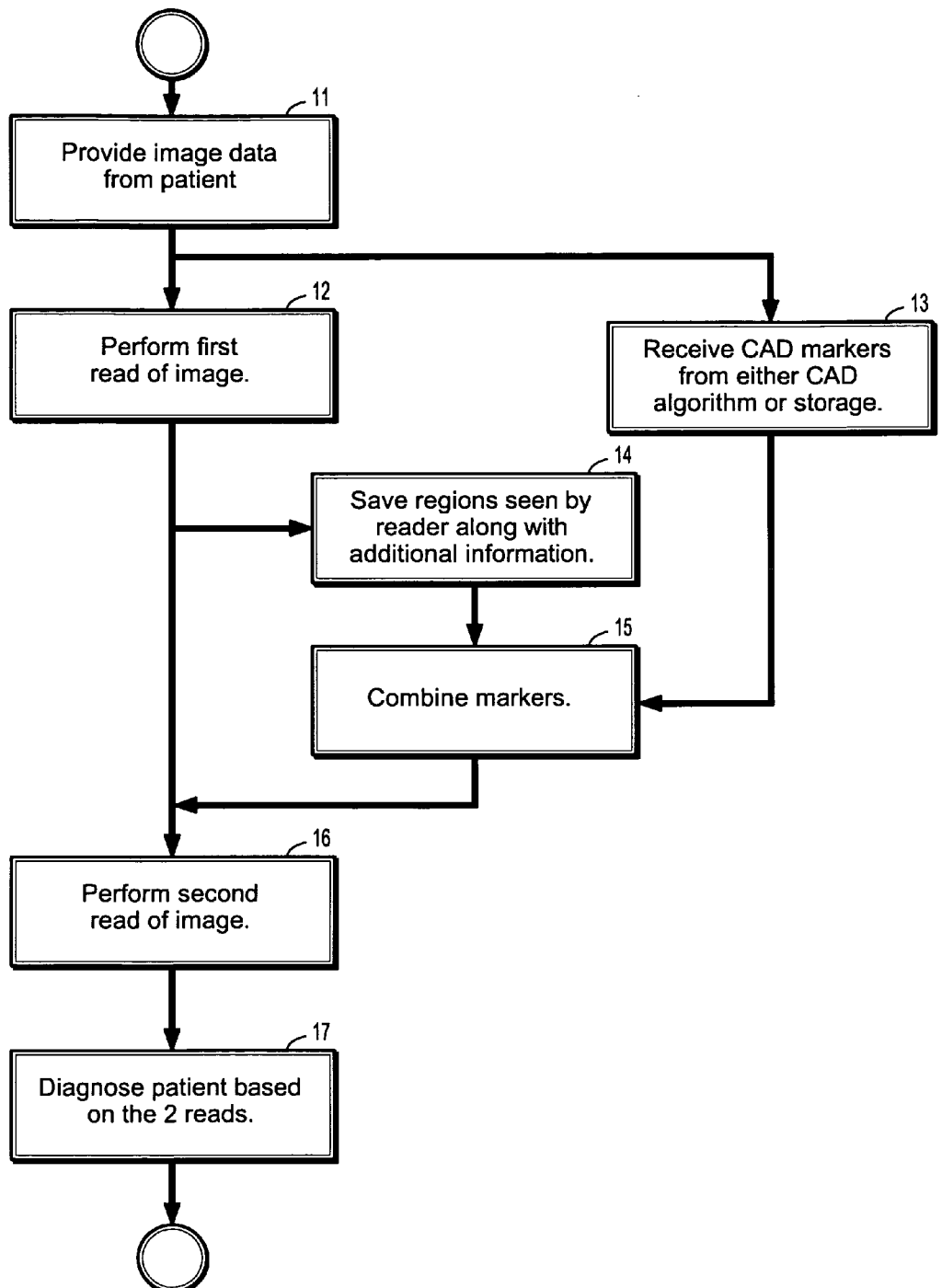
FIG. 1 is a flow chart of a method for the smart display of CAD results, according to an embodiment of the invention.

Exemplary embodiments of the invention as described herein generally include systems and methods for the smart display of CAD markers using first read knowledge. However, specific structural and functional details disclosed herein are merely representative for purposes of describing example embodiments of the present invention. This invention may, however, be embodied in many alternate forms and should not be construed as limited to the embodiments set forth herein.

Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present invention. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (i.e., "between" versus "directly between", "adjacent" versus "directly adjacent", etc.).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes" and/or "including", when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved.

As used herein, the term "image" refers to multi-dimensional data composed of discrete image elements (e.g., pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, the methods of the inventions are not limited to such images, and can be applied to images of any dimension, e.g. a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

A flow chart of a method according to an embodiment of the invention for the smart display of CAD results is shown in FIG. 1. Referring now to the figure, image data from a patient is received at step 11. The image data can be a raw, unprocessed image, or it could be an image that has undergone processing, such as segmentation and identification of objects. The image data can be acquired according to any imaging modality as is known in the art, such as computed tomography (CT), magnetic resonance imaging (MRI), positron emission tomography (PET), ultrasound (US), etc. The image data can be scalar valued intensities, or vector values, such as colorized images. At step 12, the patient data is first reviewed by a reader, such as a physician, in a first read. Typically, the image data will be displayed to the reader on a display monitor of a computer workstation as either 2-dimensional slices of the 3-dimensional image, or as a rendering of a projection of the image, or selected objects within the image, into the 2-dimensional display. The image regions reviewed by the reader are marked and stored separately at step 14. The saved markers include indicators to the region location in the image, and can optionally include other information as well, such as the amount of time the reader spent reviewing the marked region before saving it and the window-levels used for reviewing the region. Alternatively, the actual regions reviewed by the reader can be stored. For example, in cases where renderings of images or objects are used for diagnosis, the parts of the images or objects visible to the user can be stored. In cases where 2-dimensional images are used for review, user interactions with the image such as zooming, panning, etc. can be used to determine the region reviewed. Eye-tracking techniques can also be employed to determine the region reviewed as well as the time spent on reviewing. An exemplary, non-limiting method of marking includes having the reader select a region with a mouse or other pointing device. The reader can either use the pointing device to select a region, or click on a point within a region, in which case a sub-volume surrounding the click point will be selected.

The patient image data can be supplied as input to a CAD algorithm at step 13. Many CAD methods are well known in the art. Exemplary, non-limiting algorithms include colonic polyp detection, pulmonary nodule detection, breast-lesion detection, liver-lesion detection, etc. The output of the CAD algorithm is a set of markers of locations within the image. Alternatively, the image data could have been supplied to the CAD algorithm at an earlier time, or it could have been supplied to a third party for a CAD analysis. In these cases, the CAD output would be stored, and step 13 would only involve reading these CAD markers form storage. These markers are combined at step 15 with the reader-selected markers from the first read and stored at step 14, and the combined set of markers is categorized for presentation to the reader. The categorized list of markers is then presented to the reader for a second read at step 16. The list can be presented as a sorted list in a drop down menu for the reader to select a marker for review, or the marked locations can be sequentially presented to the reader in an order determined by the categorization of the markers. The reader reviews the markers from the two reads at step 17 to complete a diagnosis based on the patient data. There are many different reasons for sorting the markers shown to the user. For certain applications, the user might be interested in only one positive marker. Sorting the markers presents a higher probability that the user reviews the positive markers first, decreasing the time spent on the diagnosis.

There are many ways to categorize the markers. One exemplary, non-limiting method is to determine whether or not a region pointed to by a given CAD marker was seen by the reader during the first read. The markers can be sorted into a first set and a second set by this criteria. The first set of markers are to those locations that were not detected during the first read, while the second set of markers are to those locations already detected during the first read. The first set of markers can be displayed to the reader first. This split of the markers set into two sets enables the reader to spend more time on markers not previously detected, and less time on those already detected in the first read. This can lead to a reduction of diagnostic time during the second read.

Another exemplary, non-limiting method of categorizing the markers is to sort them according to the amount of time spent by the reader in reviewing the marked locations during the first read. For this, not only is the region seen by the reader during the first read stored, but also the amount of time spent by the reader in reviewing each region. Using this information, the markers are sorted based on how much time the reader spent reviewing the regions surrounding or pointed to by the markers. The markers with the least amount of time are displayed first, while the markers with the most time will be displayed last. Those markers detected by the CAD algorithm and missed by the reader during the first read, will have zero time, and thus will be displayed first.

Note that the reader can optionally decide to display only those additional markers detected by the CAD algorithm, or alternatively, display only those markers detected by both the CAD algorithm and the first read.

Methods according to an embodiment of the invention can be incorporated into any system that presents results for a CAD algorithm to a reader or physician. These systems include any diagnostic system that includes CAD algorithms and presents the results to the physician after the CAD-independent first read.

In additional, the ability to display only incremental findings may be paired by selectively enabling the application to visit also those findings which were also found by the physicians. This ability to selectively review the common findings may find applications in a teaching environment whereby a medical student may first try to locate lesions, then observe the incremental findings presented by the CAD Algorithm and finally review the agreement findings with CAD. Those could be used, by a supervising physician, as a means to accelerate the learning proficiency of the medical student.

It is to be understood that various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

Furthermore, it is to be understood that the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 2:
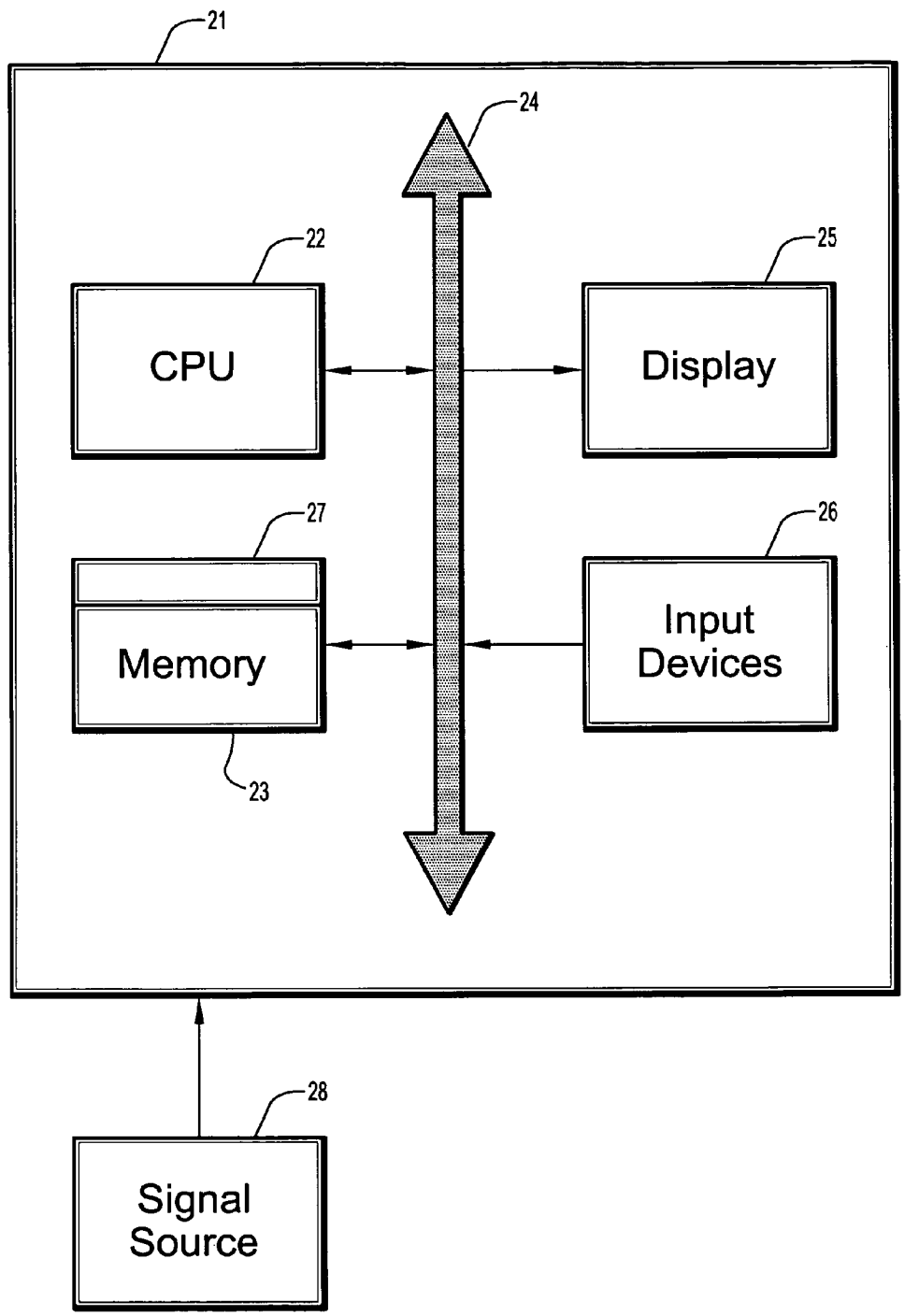
FIG. 2 is a block diagram of an exemplary computer system for implementing a method for the smart display of CAD results according to an embodiment of the invention.

Accordingly, FIG. 2 is a block diagram of an exemplary computer system for implementing a method for the smart display of CAD results according to an embodiment of the invention. Referring now to FIG. 2, a computer system 21 for implementing the present invention can comprise, inter alia, a central processing unit (CPU) 22, a memory 23 and an input/output (I/O) interface 24. The computer system 21 is generally coupled through the I/O interface 24 to a display 25 and various input devices 26 such as a mouse and a keyboard. The support circuits can include circuits such as cache, power supplies, clock circuits, and a communication bus. The memory 23 can include random access memory (RAM), read only memory (ROM), disk drive, tape drive, etc., or a combinations thereof. The present invention can be implemented as a routine 27 that is stored in memory 23 and executed by the CPU 22 to process the signal from the signal source 28. As such, the computer system 21 is a general purpose computer system that becomes a specific purpose computer system when executing the routine 27 of the present invention.

The computer system 21 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to a preferred embodiment, those skilled in the art will appreciate that various modifications and substitutions can be made thereto without departing from the spirit and scope of the invention as set forth in the appended claims.

What is claimed is:

1. A method for automatically sorting and displaying computer aided detection markers for a digitized image comprising the steps of:
   acquiring at least one digitized image, the at least one digitized image including a plurality of intensities corresponding to a domain of points on a 3-dimensional grid;
   receiving a first set of locations of interest and creating a first set of markers at the first set of locations of interest;
   automatically applying a computer-aided detection (CAD) algorithm to the at least one digitized image and receiving a second set of markers of locations of interest on the same at least one digitized image from the CAD algorithm;
   combining said first set of markers with said second set of markers to form a combined set of markers;
   automatically sorting said combined set of markers according to a predetermined criteria, wherein sorting said combined set of markers includes automatically selecting a primary set of markers, the primary set of markers including those markers detected by said CAD algorithm that are not included in said first set of markers, automatically selecting a secondary set of markers, the secondary set of markers including those markers detected by said CAD algorithm that are also included in said first set of markers, and
   presenting to a user the primary set of markers prior to the secondary set of markers during a second read of said at least one digitized image.

2. The method of claim 1, further comprising storing said first set of markers for comparison with said second set of markers.

3. The method of claim 1, further comprising performing a diagnosis based on said sorted set of markers.

4. The method of claim 1, further comprising recording the time a user spends reviewing each of said first set of markers.

5. The method of claim 4, wherein sorting said combined set of markers comprises
   sorting the second set of markers according to amount of time spent reviewing a corresponding marker in said first set of markers, and
   presenting first those markers with the least amount of time.

6. The method of claim 4, wherein the time spent reviewing said first set of markers is determined based on the user's interaction with the locations of interest marked by said markers, including using one or more of zooming, panning, and eye-tracking tools.

7. The method of claim 1, further comprising displaying said image and said markers on a display monitor.

8. The method of claim 1, further comprising storing the region reviewed during the first read.

9. The method of claim 8, wherein sorting said combined set of markers comprises
   selecting a primary set of markers from said second set of markers comprising those markers detected by said CAD algorithm that are pointing to a region of interest not reviewed during the first read,
   selecting a secondary set of markers from said second set of markers comprising those markers that are detected by said CAD algorithm that are pointing to a region of interest reviewed during the first read, and presenting said primary set of markers before said secondary set of markers.

10. The method of claim 8, wherein the reviewed region is detected based on the user's interaction with the locations of interest marked by said markers, including using one or more of zooming, panning, and eye-tracking tools.

11. The method of claim 1, further comprising presenting for display only those additional markers that were detected by said CAD algorithm.

12. The method of claim 1, further comprising presenting for display only those markers detected by said CAD algorithm that were also detected in the first read.

13. A program storage device readable by a computer, tangibly embodying a program of instructions executable by the computer to perform the method steps for displaying computer aided detection markers from a digitized image comprising the steps of:
providing a digitized image comprising a plurality of intensities corresponding to a domain of points on a 3-dimensional grid;
marking a first set of locations of interest during a first read of said image, producing a first set of markers;
receiving a second set of markers of locations of interest on the same image from a CAD algorithm;
combining said first set of markers with said second set of markers;
sorting said combined set of markers according to a predetermined criteria, wherein sorting said combined set of markers includes selecting a primary set of markers from said second set of markers comprising those markers detected by said CAD algorithm that are not included in said first set of markers, selecting a secondary set of markers from said second set of markers comp6sing those markers detected by said CAD algorithm that are also included in said first set of markers, and presenting said primary set and secondary set of markers, where the primary set of markers are presented before said secondary set of markers; and
presenting said sorted set of markers to a user for a second read of said image.

14. The computer readable program storage device of claim 13, the method further comprising storing said first set of markers for comparison with said second set of markers.

15. The computer readable program storage device of claim 13, the method further comprising performing a diagnosis based on said sorted set of markers.

16. The computer readable program storage device of claim 13, the method further comprising recording the time a user spends reviewing each of said first set of markers.

17. The computer readable program storage device of claim 16, wherein sorting said combined set of markers comprises
sorting the second set of markers according to amount of time spent reviewing a corresponding marker in said first set of markers, and
presenting first those markers with the least amount of time.

18. The computer readable program storage device of claim 16, wherein the time spent reviewing said first set of markers is determined based on the user's interaction with the locations of interest marked by said markers, including using one or more of zooming, panning, and eye-tracking tools.

19. The computer readable program storage device of claim 13, the method further comprising displaying said image and said markers on a display monitor.

20. The computer readable program storage device of claim 13, the method further comprising storing the region reviewed during the first read.

21. The computer readable program storage device of claim 20, wherein sorting said combined set of markers comprises
selecting a primary set of markers from said second set of markers comprising those markers detected by said CAD algorithm that are pointing to a region of interest not reviewed during the first read,
selecting a secondary set of markers from said second set of markers comprising those markers that are detected by said CAD algorithm that are pointing to a region of interest reviewed during the first read, and
presenting said primary set of markers before said secondary set of markers.

22. The computer readable program storage device of claim 20, wherein the reviewed region is detected based on the user's interaction with the locations of interest marked by said markers, including using one or more of zooming, panning, and eye-tracking tools.

23. The computer readable program storage device of claim 13, the method further comprising presenting for display only those additional markers that were detected by said CAD algorithm.

24. The computer readable program storage device of claim 13, the method further comprising presenting for display only those markers detected by said CAD algorithm that were also detected in the first read.

* * * * *